US009060898B2

(12) United States Patent
Hoshika

(10) Patent No.: US 9,060,898 B2
(45) Date of Patent: Jun. 23, 2015

(54) MANUFACTURING DEVICE FOR ABSORBENT BODY AND MANUFACTURING METHOD THEREFOR

(75) Inventor: Kazuhiko Hoshika, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 13/983,483

(22) PCT Filed: Jan. 27, 2012

(86) PCT No.: PCT/JP2012/051795
§ 371 (c)(1), (2), (4) Date: Oct. 11, 2013

(87) PCT Pub. No.: WO2012/105443
PCT Pub. Date: Aug. 9, 2012

(65) Prior Publication Data

US 2014/0027943 A1 Jan. 30, 2014

(30) Foreign Application Priority Data

Feb. 4, 2011 (JP) ................................ 2011-023097

(51) Int. Cl.
*A61F 13/15* (2006.01)

(52) U.S. Cl.
CPC ..... *A61F 13/15617* (2013.01); *A61F 13/15658* (2013.01)

(58) Field of Classification Search
None
See application file for complete search history.

(56) References Cited

U.S. PATENT DOCUMENTS 5,102,585 A * 4/1992 Pieper et al. ............... 264/37.29
5,350,597 A * 9/1994 Pelley .......................... 427/197
6,207,099 B1 * 3/2001 Rooyakkers et al. ......... 264/518
7,303,708 B2 * 12/2007 Andrews et al. .............. 264/121

FOREIGN PATENT DOCUMENTS

JP 7289589 A 11/1995
JP 9503691 A 4/1997
JP 2008-284182 A 11/2008
JP 2009-112347 A 5/2009
JP 2009-114555 A 5/2009

OTHER PUBLICATIONS

Corresponding WO 2012/105443 A1 International Search Report dated Apr. 24, 2012.
Office Action mailed Oct. 28, 2014, corresponding to Japanese patent application No. 2011-023097.

* cited by examiner

*Primary Examiner* — Mary F Theisen
(74) *Attorney, Agent, or Firm* — Lowe Hauptman & Ham, LLP

(57) ABSTRACT

A device for manufacturing an absorbent body by depositing on a deposit portion liquid absorbent fiber contained in a first gas flowing through a duct. The device for manufacturing an absorbent body includes the deposit portion that travels along a predetermined travel path, the duct that distributes the liquid absorbent fiber from a distribution opening placed opposing the travel path, a particulate matter discharge tube, a tip end thereof being introduced into the duct, that discharges a second gas having particulate matter mixed therein from a discharge hole of the tip end, and an operable throttle portion that throttles a flow path of the particulate matter discharge tube to change discharge distribution of the particulate matter. The operable throttle portion is operated in conjunction with the travel of the deposit portion.

14 Claims, 12 Drawing Sheets

HORIZONTAL DIRECTION
UP
VERTICAL DIRECTION
DOWN
AIR SUCTION
AIR SUCTION
PART VI

B-B CROSS SECTION

MANUFACTURING DEVICE FOR ABSORBENT BODY AND MANUFACTURING METHOD THEREFOR

RELATED APPLICATIONS

The present application is a National Phase of PCT/JP2012/051795, filed Jan. 27, 2012, and is based on, and claims priority from, Japanese Application No. 2011-023097 filed Feb. 4, 2011.

TECHNICAL FIELD

The present invention relates to a manufacturing device for absorbent bodies relating to absorbent articles such as disposable diapers and the like and a manufacturing method therefor.

BACKGROUND ART

Disposable diapers and sanitary napkins are conventionally known as absorbent articles that absorb fluid such as excreted fluids and the like.

This absorbent article includes an absorbent body 1 that absorbs fluid. The absorbent body 1 is produced by forming liquid absorbent fiber such as pulp fibers 2, as a main material, into a predetermined shape. Generally, this absorbent body 1 has superabsorbent polymer (which is high molecular weight polymer and the like having high fluid retaining performance by swelling and the like due to fluid absorption, and is referred to as SAP hereunder) mixed therein as an example of particles. Such an absorbent body 1 has a longitudinal direction and a width direction orthogonal to each other and a thickness direction as well. Among these, the longitudinal direction and the width direction are parallel to the longitudinal direction and the width direction of disposable diapers and sanitary napkins, respectively.

Such absorbent body 1 is for example, is manufactured using a rotating drum 120 that rotates about a rotational axis C120 along a CD direction (the direction perpendicular to the plane of the paper in FIG. 1A, as shown in a schematic diagram of FIG. 1A. On the outer circumferential face of this rotating drum 120, a forming die 121 having a shape corresponding to the outer shape of the absorbent body 1 is provided, and multiple air intake holes (not shown) are formed in the forming die 121. Additionally, a duct 131 is arranged facing the predetermined position in the circumferential direction Dc of the rotating drum 120. In this duct 131, pulp fiber 2 flows along the airflow 3. Further, a tip end of a polymer discharge tube 141 is introduced into the duct 131, and SAP is discharged from a discharge hole 141*a* of the above tip end into the duct 131.

Therefore, when the above-mentioned forming die 121 passes the location of the duct 131, the pulp fiber 2 and SAP are deposited on the forming die 121 by air intake through the air intake holes of the forming die 121, thereby forming the absorbent body 1 whose longitudinal direction is the circumferential direction Dc of the rotating drum 120.

Here, the pulp fiber 2 and SAP are required to be deposited in a predetermined distribution state.

With regard to this point, PTL1 discloses a method of distributing SAP evenly in the width direction (CD direction) of the absorbent body 1. In other words, as shown in an enlarged view of FIG. 1B, PTL1 discloses that a distribution plate 143 is placed on the outer side of the discharge hole 141*a* of the polymer discharge tube 141, and SAP flowing along the airflow 6 in the above discharge tube 141 is made to collide with the distribution plate 143 to discharge SAP into the duct 131 in a distributed manner.

CITATION LIST

Patent Literature

[PTL 1]

Japanese Patent Application Laid-open Publication No. 2009-112347

SUMMARY OF THE INVENTION

Technical Problem

Depending on the types and specifications of absorbent articles, there are cases where it is desired to change SAP distribution in the width direction in accordance with the location of the longitudinal direction of the absorbent body 1. For example, there are cases where it is desired, while a crotch corresponding portion 1*c* of the absorbent body 1 causes SAP to be collected at the central portion of the width direction, a front body corresponding portion 1*e* and a back body corresponding portion 1*e* adjacent longitudinal back and forth thereof causes SAP to be distributed substantially evenly in the width direction (FIG. 5A).

Further, in the case where the outer shape of the absorbent body 1 is a substantially sandglass shape when viewed from above, the size in the CD direction of the crotch corresponding portion 21*c* as a central portion 21*c* of the circumferential direction Dc in the forming die 121 is narrower than the size in the CD direction of the front body corresponding portion 21*e* and the back body corresponding portion 21*e* as both end portions 21*e*, 21*e* of the above circumferential direction Dc (FIG. 5B). Therefore, it is understood that when the discharge distribution itself of SAP in the CD direction which is discharged from the polymer discharge tube 141 is made to be a substantially uniform distribution along the CD direction in the front body corresponding portion 21*e* and the back body corresponding portion 21*e*, but is made to be a distribution collected at the center in the CD direction in the crotch corresponding portion 21*c*, the amount of SAP that fails to be deposited on the crotch corresponding portion 21*c* can be reduced and SAP can be certainly deposited on the above crotch corresponding portion 21*c*.

However, it is understood that, since the discharge distribution of SAP in the width direction can not be changed in accordance with the travel of the forming die 121 in the circumferential direction Dc with the method using the above-mentioned distribution plate 143, it is difficult to handle these needs.

The present invention has been made in view of the above conventional problems, and an advantage thereof is to allow the discharge distribution of the particulate matter to be changed in accordance with the travel of the deposit portion, when the absorbent body is produced by depositing liquid absorbent fiber such as pulp fiber flowing in the duct and particulate matter such as SAP, to the deposit portion such as a forming die.

Solution to Problem

A principal aspect of the invention for achieving the above advantage is a device for manufacturing an absorbent body by depositing on a deposit portion liquid absorbent fiber contained in a first gas flowing through a duct, comprising:

the deposit portion that travels along a predetermined travel path;

the duct that distributes the liquid absorbent fiber from a distribution opening placed opposing the travel path;

a particulate matter discharge tube, a tip end thereof being introduced into the duct, that discharges a second gas having particulate matter mixed therein from a discharge hole of the tip end; and an operable throttle portion that throttles a flow path of the particulate matter discharge tube to change discharge distribution of the particulate matter, the operable throttle portion being operated in conjunction with the travel of the deposit portion.

Further, a method of manufacturing an absorbent body by depositing on a deposit portion liquid absorbent fiber contained in a first gas flowing through a duct, comprising:

allowing the deposit portion to travel a predetermined travel path;

distributing the liquid absorbent fiber from a distribution opening of the duct which is placed opposing the travel path;

discharging a second gas having particulate matter mixed therein from a discharge hole of a tip end of a particulate matter discharge tube, the tip end being introduced into the duct; and allowing an operable throttle portion to be operated in conjunction with the travel of the deposit portion, the operable throttle portion throttling a flow path of the particulate matter discharge tube to change discharge distribution of the particulate matter.

Other features of the present invention will become apparent from the description in this specification and the attached drawings.

Effects of the Invention

According to the invention, when the absorbent body is produced by depositing liquid absorbent fiber such as pulp fiber flowing in the duct and particulate matter such as SAP, on the deposit portion such as a forming die, the discharge distribution of particulate matter can be changed in accordance with the travel of the deposit portion.

BRIEF DESCRIPTION OF DRAWINGS

[FIG. 1]

[FIG. 2]

FIG. 3A is a schematic vertical cross-sectional view of a manufacturing device 10 for the absorbent body 1 of the first embodiment.

FIG. 3B is a developed view of an outer circumferential face 20*a* of a rotating drum 20 included in the above manufacturing device 10.

FIG. 4 is a vertical cross-sectional view of the polymer discharge tube 41.

[FIG. 5]

[FIG. 6]

[FIG. 7]

[FIG. 8]

FIG. 9 is a perspective view of a portion proximate the discharge hole 41*a* of the polymer discharge tube 41.

[FIG. 10]

[FIG. 11]

DESCRIPTION OF EMBODIMENTS

Figure 1A:
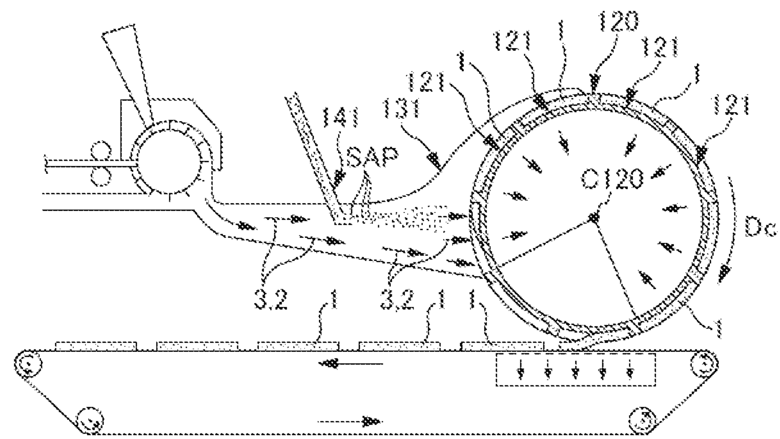
FIG. 1A is a schematic diagram of a conventional manufacturing device for an absorbent body 1.
Figure 1B:
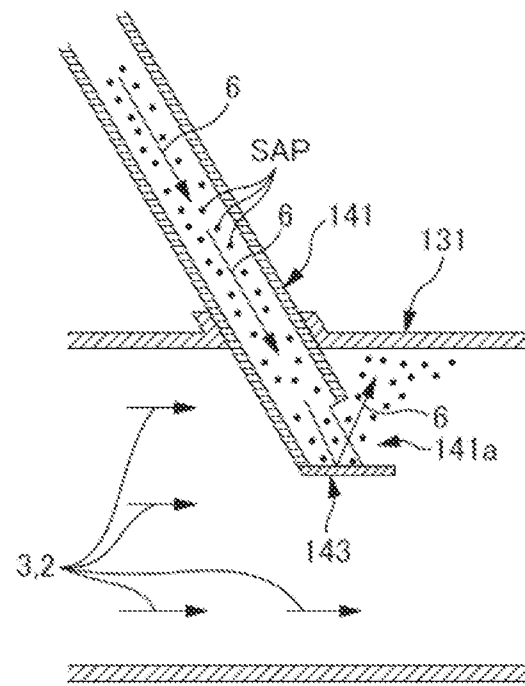
FIG. 1B is an enlarged view of a portion proximate the discharge hole 141*a* of the polymer discharge tube 141.

At least the following matters will be made clear by the description in the present specification and the accompanying drawings.

A device for manufacturing an absorbent body by depositing on a deposit portion liquid absorbent fiber contained in a first gas flowing through a duct, comprising:

the deposit portion that travels along a predetermined travel path;

the duct that distributes the liquid absorbent fiber from a distribution opening placed opposing the travel path;

a particulate matter discharge tube, a tip end thereof being introduced into the duct, that discharges a second gas having particulate matter mixed therein from a discharge hole of the tip end; and an operable throttle portion that throttles a flow path of the particulate matter discharge tube to change discharge distribution of the particulate matter, the operable throttle portion being operated in conjunction with the travel of the deposit portion.

With such a device for manufacturing an absorbent body, since the operable throttle portion is operated in conjunction with the travel of the deposit portion, the discharge distribution of the particulate matter can be changed in accordance with the travel of the deposit portion.

In such a device for manufacturing an absorbent body, it is desirable that the operable throttle portion includes a duct portion at which a sectional shape of the flow path can be changed, the sectional shape of the flow path is changed in conjunction with the travel of the deposit portion.

With such a device for manufacturing an absorbent body, since the sectional shape of the flow path is changed in conjunction with the travel of the deposit portion, the discharge distribution of the particulate matter can be changed in conjunction with the travel of the deposit portion.

In such a device for manufacturing an absorbent body, it is desirable that the operable throttle portion includes a protrusion protrudably guided inward into the flow path of the duct portion, the sectional shape of the flow path is changed by changing a protruding length of the protrusion into the flow path.

With such a device for manufacturing an absorbent body, the discharge distribution of the particulate matter can be changed by changing the protruding length of the protrusion.

In such a device for manufacturing an absorbent body, it is desirable that the operable throttle portion includes a duct portion having a sectional shape of the flow path other than a perfect circular shape, the duct portion rotates about a duct axis of the duct portion in conjunction with the travel of the deposit portion.

With such a device for manufacturing an absorbent body, the sectional shape of the flow path of the duct portion is a shape other than a perfect circular shape. Further, the duct portion rotates about the duct axis in conjunction with the travel of the deposit portion. Therefore, the discharge distribution of the particulate matter can be changed in conjunction with the travel of the deposit portion based on the above rotation.

In such a device for manufacturing an absorbent body, it is desirable that, at the travel path, a plurality of the deposit portions travels at a predetermined pitch along the travel path, the operable throttle portion repeats a given unit motion as the operation each time the deposit portion passes by the position of the duct.

With such a device for manufacturing an absorbent body, since the operable throttle portion repeats the same unit motions for each deposit portion, the discharge distribution of the particulate matter can be changed in a same manner with respect to each of the deposit portions.

In such a device for manufacturing an absorbent body, it is desirable that the operable throttle portion is provided outside the duct.

With such a device for manufacturing an absorbent body, since the operable throttle portion is provided to the outside of the duct, maintenance and inspection of the operable throttle portion can be easily performed.

Further, since the operable throttle portion is provided to the outside of the duct, even if the operable portion of the operable throttle portion protrudes outside of the particulate matter discharge tube, the motion of the operable portion of the operable throttle portion does not affect the flow of the first gas in the duct. As a result, it is possible to eliminate the influence on the deposition of liquid absorbent fiber.

Further, a method of manufacturing an absorbent body by depositing on a deposit portion liquid absorbent fiber contained in a first gas flowing through a duct, comprising:

allowing the deposit portion to travel a predetermined travel path;

distributing the liquid absorbent fiber from a distribution opening of the duct which is placed opposing the travel path;

discharging a second gas having particulate matter mixed therein from a discharge hole of a tip end of a particulate matter discharge tube, the tip end being introduced into the duct; and allowing an operable throttle portion to be operated in conjunction with the travel of the deposit portion, the operable throttle portion throttling a flow path of the particulate matter discharge tube to change discharge distribution of the particulate matter.

With such a method of manufacturing an absorbent body, since the operable throttle portion is operated in conjunction with the travel of the deposit portion, the discharge distribution of the particulate matter can be changed in accordance with the travel of the deposit portion.

===First Embodiment===

A manufacturing device 10 and a manufacturing method for an absorbent body 1 according to the first embodiment are used for manufacturing the absorbent body 1 of disposable diapers and sanitary napkins as an example of the absorbent article.

Figure 2A:
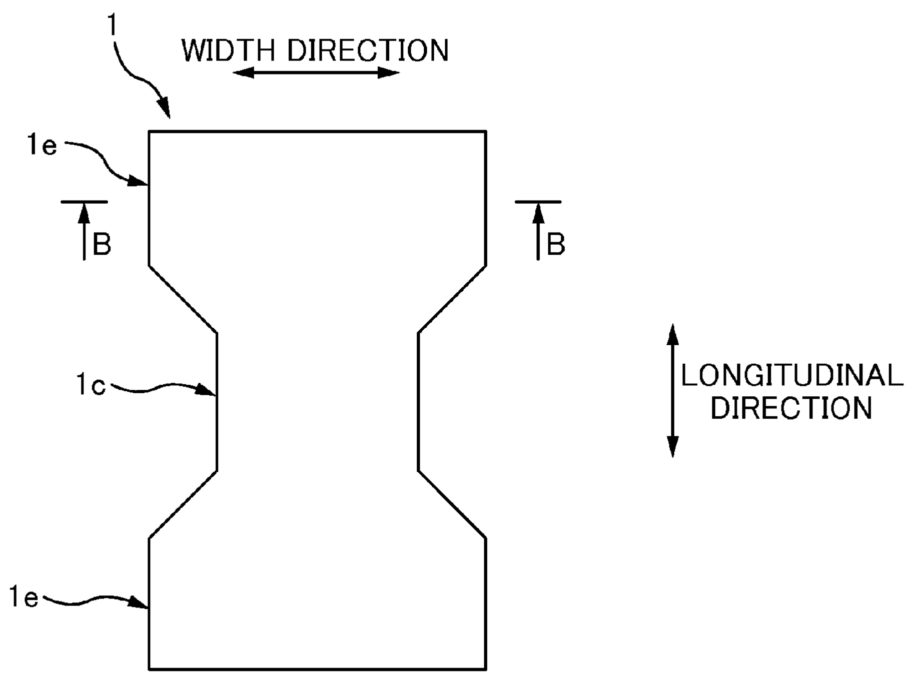
FIG. 2A is a schematic plan view of the absorbent body 1.
Figure 2B:
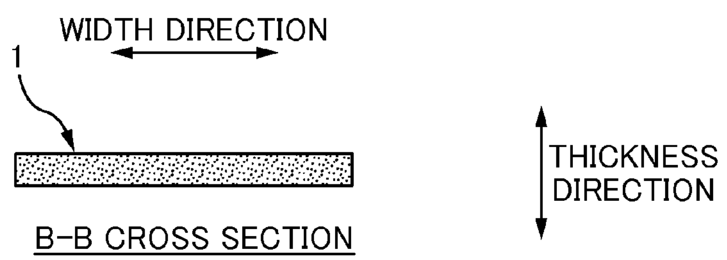
FIG. 2B is a cross-sectional view taken along line B-B of FIG. 2A.

FIG. 2A is a schematic plan view of the absorbent body 1, and FIG. 2B is a cross-sectional view taken along line B-B in FIG. 2A.

The absorbent body 1 is produced by laminating pulp fiber as an example of liquid absorbent fiber and SAP (superabsorbent polymer) as an example of particulate matter into a predetermined outer shape in a thickness direction with the pulp fiber and SAP mixed. In this example, the outer shape is, for example, a substantially sandglass shape when viewed from above. In other words, a central portion 1*c* in the longitudinal direction of the absorbent body 1 has a constricted shape in the width direction than both end portions 1*e*, 1*e* in the longitudinal direction. However, the outer shape is not limited thereto. For example, the outer shape may be a substantially rectangular shape when viewed from above.

Figure 3A:
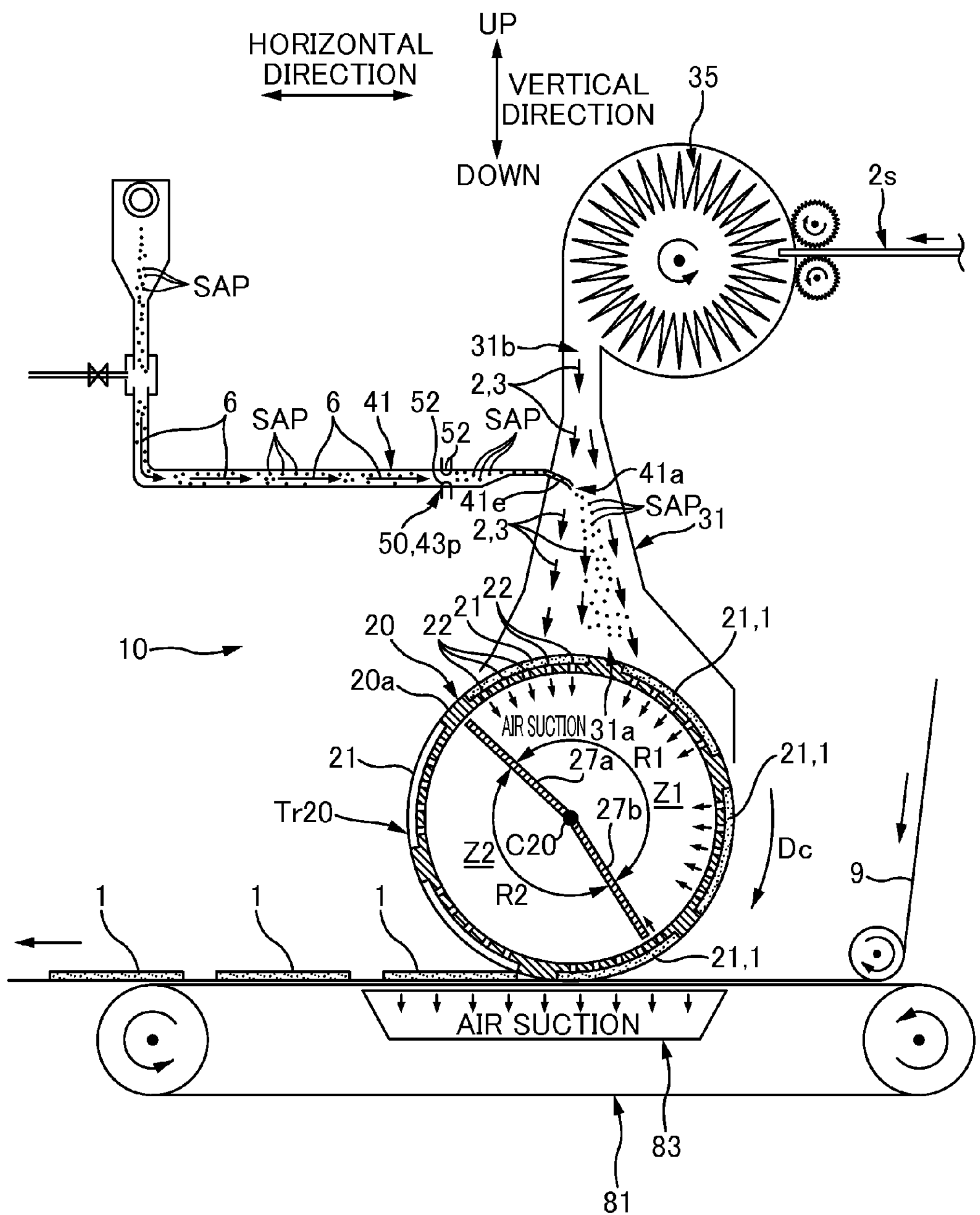
[FIG. 3A]
Figure 3B:
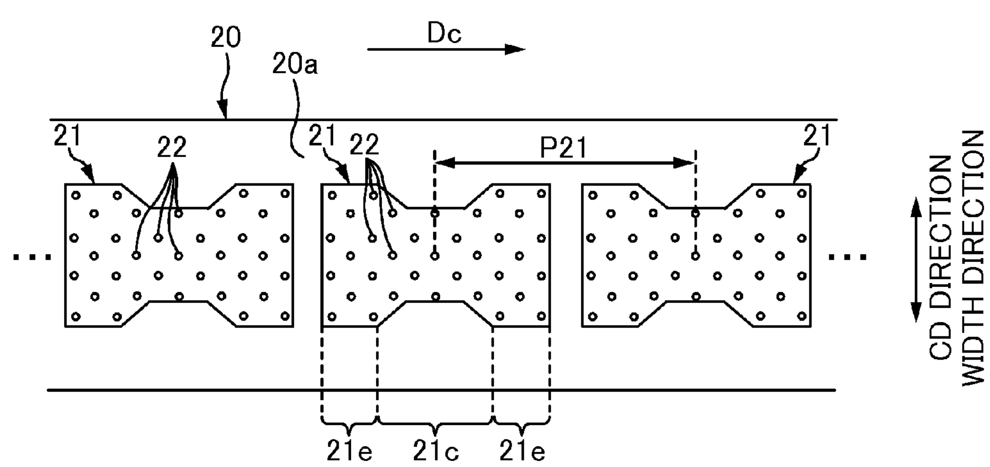
[FIG. 3B]

FIG. 3A is a schematic vertical cross-sectional view of the manufacturing device 10 of the absorbent body 1. Further, FIG. 3B is a developed view showing an outer circumferential face 20*a* of a rotating drum 20 included in the above manufacturing device 10.

The manufacturing device 10 for the absorbent body 1 according to the first embodiment is a so-called fiber stacking device 10. In other words, this manufacturing device 10 includes a rotating drum 20 that is provided with a forming die (corresponding to the deposit portion) in a depressed form on the outer circumferential face 20*a* thereof and that rotates in the circumferential direction Dc, a duct 31 that distributes pulp fiber 2 toward the outer circumferential face 20*a* of the rotating drum 20 to deposit pulp fiber 2 in the forming die 21 and form the absorbent body 1, and a belt conveyor 81 that is positioned on the downstream side of the duct 31 in the circumferential direction Dc than the location at which the duct 31 is set, to convey the absorbent body 1 released from the forming die 21.

Note that in the description below, the circumferential direction Dc of the rotating drum 20 is also referred to as simply the "circumferential direction Dc" and the width direction of the rotating drum 20 (the direction perpendicular to the plane of the paper in FIG. 3A) is also referred to as the "CD direction" or the "left/right direction". Additionally, any direction within the plane intersecting this CD direction is also referred to as the "MD direction" and, for example, the circumferential direction Dc is a part of the MD direction, the direction of the duct axis of the duct 31 is also a part of the MD direction, and the direction of the duct axis of the later described polymer discharge tube 41 is also a part of the MD direction.

The rotating drum 20 has as its main body, a cylindrical body that is driven and rotates in the clockwise direction as one direction, about for example, a horizontal rotational axis C20 along the CD direction. By driving the rotating drum 20 to rotate, the outer circumferential face 20*a* of the rotating drum travels along a predetermined circumferential path Tr 20 (corresponding to the travel path). On the outer circumferential face 20*a*, a plurality of forming dies 21, 21 . . . are provided at a predetermined arrangement pitch P21 in the circumferential direction Dc, and these forming dies 21, 21 . . . also travel along the aforementioned circumferential path Tr 20 in an integrated manner with the aforementioned outer circumferential face 20*a*.

The outer shape of each forming die 21 is a shape in accordance with the outer shape of the aforementioned absorbent body 1, and in this example, is a substantially sandglass shape when viewed from above as shown in FIG. 3B. Further, multiple air intake holes 22, 22 . . . are formed at the bottom surface of each forming die 21. Therefore, the pulp fibers 2 in the duct 31 flow along the flow 3 of air (corresponding to the first gas) created in the duct 31 by air intake through the air intake holes 22 to be distributed and deposited in the forming die 21. Thereby, the absorbent body 1 having the substantially sandglass shape when viewed from above is formed in the forming die 21 with this direction of deposition as the thickness direction thereof, and with the circumferential direction Dc and CD direction as the longitudinal direction and width direction thereof, respectively (FIGS. 3A and 3B).

Note that, in the circumferential direction Dc, such air intake is performed in the first region R1 where the forming die 21 opposes the duct 31 but is stopped and is not performed in the second region R2 where the forming die 21 opposes the belt conveyor 81, as shown in FIG. 3A. Further, at the latter second region R2, the absorbent bodies 1 in the forming dies 21 are sequentially released from the forming dies 21 by air suction with the suction box 83 in the belt conveyor 81, and in this way the absorbent bodies 1 are transferred onto the belt conveyor 81 to be conveyed on the belt conveyor 81 thereafter. As an example of a configuration that performs the foregoing air suction, there can be given one that includes partition walls 27*a*, 27*b* that divide space at the inner circumferential side of the rotating drum 20 into zones in the circumferential direction Dc, and a blower, not shown, connected to zone Z1, between the plurality of zones Z1 and Z2, corresponding to the first region R1 at which air suction is to be performed for keeping negative pressure thereat. Note that it is a matter of course that the air intake holes 22 of the rotating drum 20 and the aforementioned space on the inner circumferential side are in communication allowing air to flow.

Further, as shown in the example of FIG. 3A, sheet form members 9 such as non-woven fabric and tissue paper can be fed on this belt conveyor 81 for the absorbent body 1 to be transferred thereon. And in this case, these sheet form members 9 become the surface sheet (the sheet that comes into contact with the wearer's skin) relating to disposable diapers and sanitary napkins.

The duct 31 is, for example, a tubular member having an approximate rectangular section and is positioned above the rotating drum 20 with the duct axis direction thereof oriented in the up-down direction (vertical direction) with regard to the MD direction, while the distribution opening 31*a* at the bottom end thereof covering over a predetermined area in the circumferential direction Dc above the outer circumferential face 20*a* of the rotating drum 20. Further, pulp fiber 2 made by pulverizing pulp sheet 2*s* by the pulverizer 35 is fed from the opening 31*b* at upper end that is an end opposite the distribution opening 31*a*, thereby creating an airflow 3 including pulp fiber 2 flowing from the upper side toward the lower side inside the duct 31. Therefore, the absorbent body 1 is formed by the deposition of the pulp fiber 2 into the forming die 21 when the forming die 21 passes by the position of the corresponding distribution opening 31*a* along with the rotation of the rotating drum 20.

Inside this duct 31, a tip end 41*e* of the polymer discharge tube 41 (corresponding to the particulate matter discharge tube) is introduced thereto for injecting SAP into the forming die 21. Air 6 (corresponding to the second gas) having SAP mixed therein flows through this polymer discharge tube 41, and SAP is discharged from the discharge hole 41*a* at the tip end 41*e* of the polymer discharge tube 41 into the duct 31 along this airflow 6.

Figure 4:
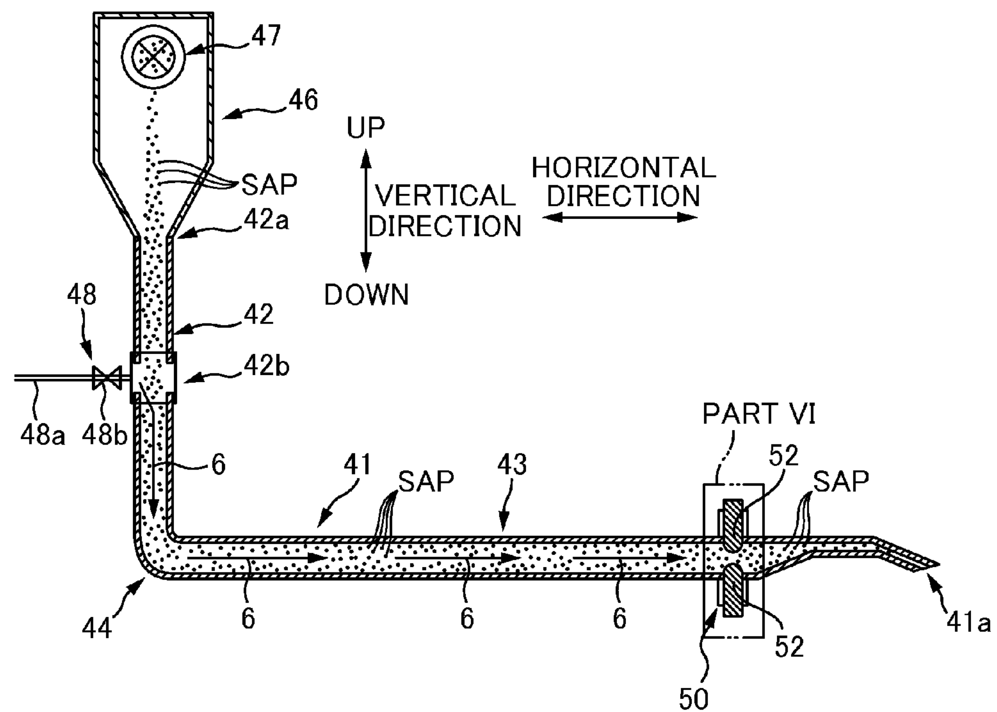
[FIG. 4]

FIG. 4 is a vertical cross-sectional view of the polymer discharge tube 41.

The polymer discharge tube 41 has a circular pipe (a cylindrical tube whose section is a perfect circle) bended in an L shape, for example, as its main body. More specifically, the polymer discharge tube 41 has a vertical duct portion 42 that has the duct axis oriented in the vertical direction to the MD direction and a horizontal duct portion 43 that has the duct axis oriented in the horizontal direction to the MD direction, and these two are connected by a bend duct 44. Further, the aforementioned discharge hole 41*a* is provided at the tip end 41*e* of the horizontal duct portion 43 whereas a SAP feed mechanism 46 for feeding SAP to polymer discharge tube 41 is provided at the upper end 42*a* of the vertical duct portion 42. The SAP feed mechanism 46 has, for example, a screw feeder 47 at the upper portion thereof and SAP is volumetrically fed by allowing SAP to drop from the screw feeder 47 to the upper end 42*a* of the vertical duct portion 42. Further, a compressed air injection device 48 is connected at approximately the middle position 42*b* of this vertical duct portion 42. Then, compressed air of a predetermined pressure is permanently injected from this compressed air injection device 48 toward the discharge hole 41*a*, thereby creating an airflow 6 along the approximately duct axis direction at the portion in the tube on the downstream side of the aforementioned approximately middle position 42*b*, to allow SAP to flow along this airflow 6 to be discharged through the discharge hole 41*a* and into the duct 31.

As an example of a configuration of this compressed air injection device 48, there can be given one that includes a tank, not shown, that stores compressed air, a pipe 48*a* that connects this tank with the vertical duct portion 42, a valve 48*b* that opens/closes the path of pipe 48*a*, and a compressor, not shown, that maintains the pressure value of the compressed air in the aforementioned tank within a predetermined range. Feeding of the compressed air into the polymer discharge tube 41 is controlled by controlling opening/closing of the valve 48*b* appropriately.

The distribution of SAP in the width direction (CD direction) in the absorbent body 1 generally aims to be uniformly distributed, and additionally, in many cases this uniform distribution is allowed to be maintained through the entire length in the longitudinal direction (circumferential direction Dc).

Figure 5A:
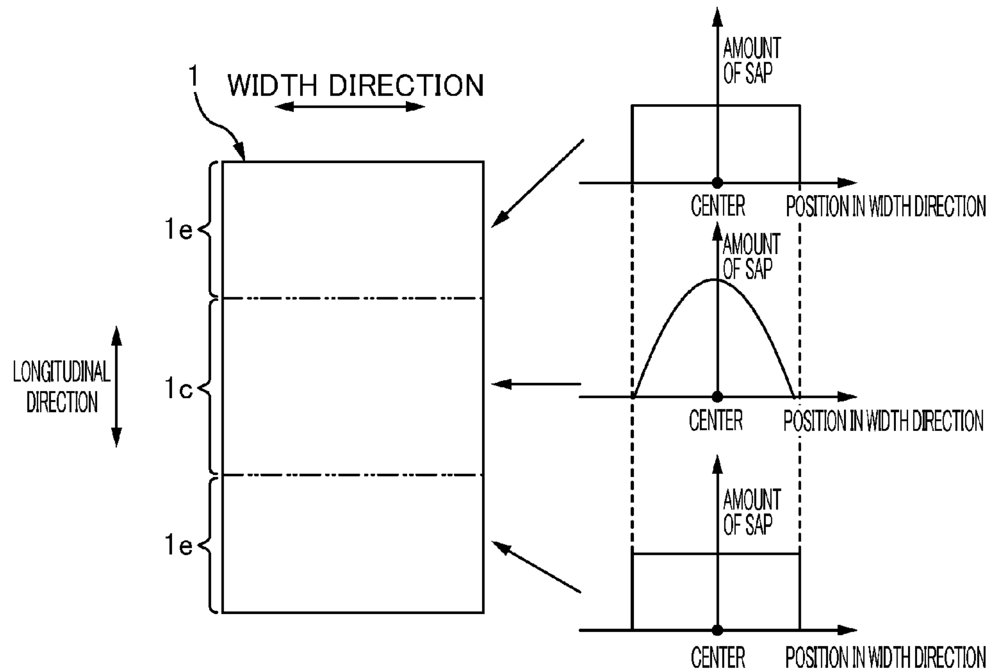
FIGS. 5A and 5B are explanatory diagrams showing needs to change the discharge distribution in the CD direction of SAP.

However, there are various specifications in disposable diapers and sanitary napkins, and liquid absorbency requested in each specification also varies. Therefore, it is considered preferable that the distribution state of SAP in the absorbent body 1 is also changed in accordance with its liquid absorbency. That is to say, depending on the specification, it is considered that there are cases it is preferable, for example, the distribution state of SAP in the CD direction (width direction) has been changed in accordance with the position of the longitudinal direction in the absorbent body 1. More specifically, as shown in FIG. 5A, for example, it is considered that there are also needs to form a distribution pattern such that SAP is distributed more densely at a central portion 21*c* of the width direction and is distributed sparsely at both sides thereof in a crotch corresponding portion 1*c* of the absorbent body 1, while SAP is substantially uniformly distributed through the entire length in the width direction in a front body corresponding portion 1*e* and a back body corresponding portion 1*e* adjacent longitudinal back and forth thereof.

Figure 5B:
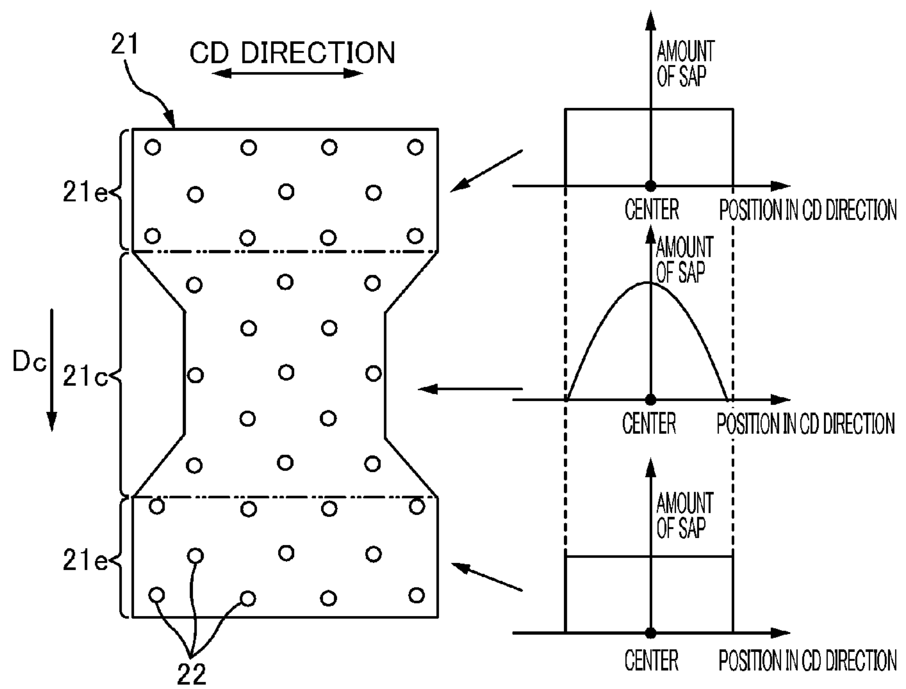

In the case where the outer shape of the absorbent body 1 is a substantially sandglass shape when viewed from above as in the first embodiment, the size in the CD direction of the crotch corresponding portion 21*c* that is a central portion of the circumferential direction Dc of the forming die 21 as shown in FIG. 3B is narrower than the size in the CD direction of the front body corresponding portion 21*e* and back body corresponding portion 21*e* that are both end portions 21*e*, 21*e* in the circumferential direction Dc. Therefore, as shown in FIG. 5B, it is considered that, when the discharge distribution itself in the CD direction of SAP is made to be a substantially uniform distribution throughout the CD direction at the front body corresponding portion 21*e* and the back body corresponding portion 21*e*, and is made to be a distribution allowing SAP to be collected at the center of the CD direction in the crotch corresponding portion 21*c*, the amount of SAP which fails to be deposited on the crotch corresponding portion 21*c* can be reduced, so that SAP is allowed to be reliably deposited on this crotch corresponding portion 21*c*.

For this reason, in the first embodiment, an operable throttle portion 50 is provided for the polymer discharge tube 41 in order to respond to such needs, as shown in FIG. 4. The discharge distribution in the CD direction of SAP is changed in accordance with the travel of the forming die 21 by allowing this operable throttle portion 50 to be operated in conjunction with the travel of the forming die 21 in the circumferential direction Dc.

Figure 6A:
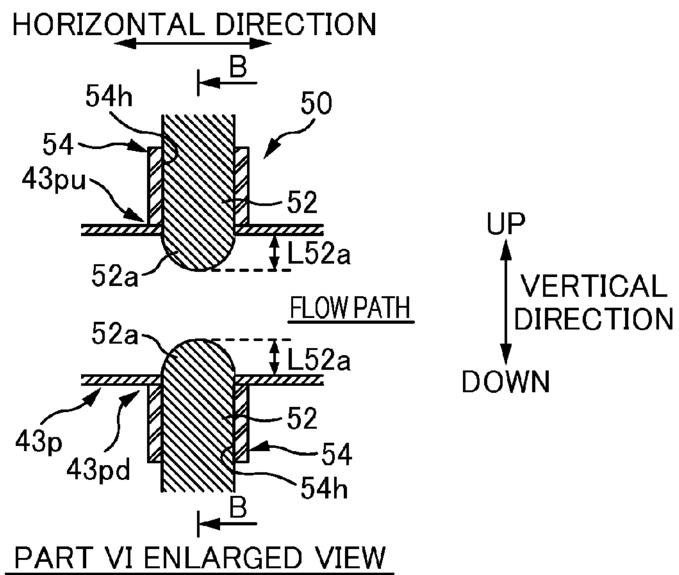
FIG. 6A is an enlarged view of part VI in FIG. 4.
Figure 6B:
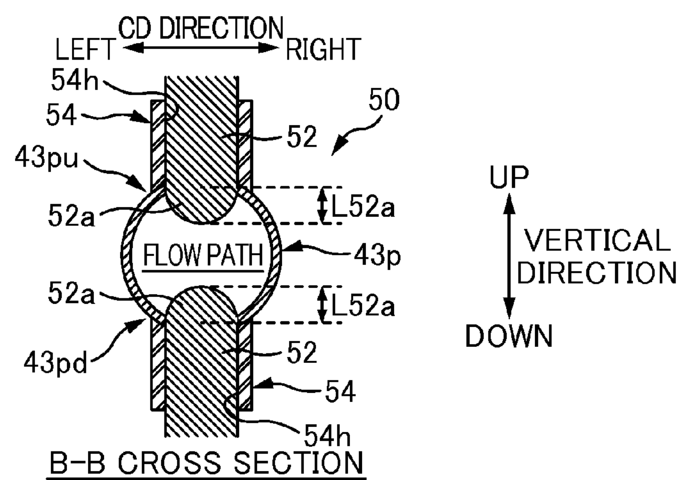
FIG. 6B is a cross-sectional view taken along line B-B of FIG. 6A.
Figure 6C:
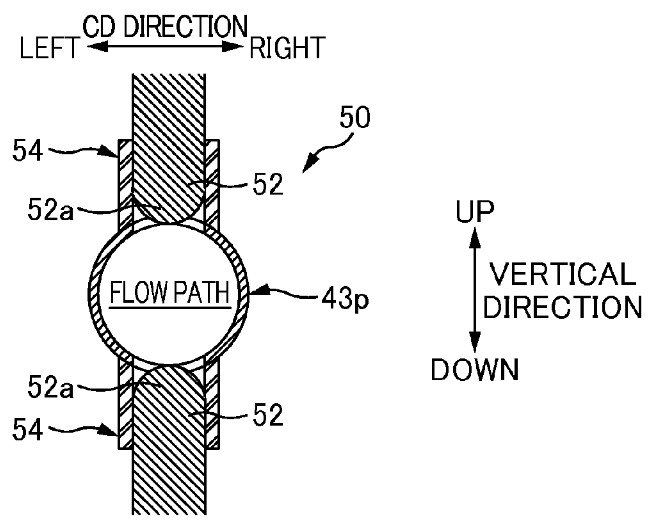
FIG. 6C is a cross-sectional view taken along line B-B of FIG. 6A in a different state from that of FIG. 6B.

FIG. 6A is an enlarged view of part VI of FIG. 4, and FIG. 6B is a cross-sectional view taken along line B-B of FIG. 6A. Further, FIG. 6C is a cross-sectional view taken along line B-B of FIG. 6A, showing a different state from FIG. 6B.

As shown in FIG. 3A, the operable throttle portion 50 is provided at a duct portion 43*p* positioned outside the duct 31 in a horizontal duct portion 43 of the polymer discharge tube 41. The operable throttle portion 50 is configured so that a flow path at the duct portion 43*p* is selectable between a state where the flow path is throttled to be narrower than the flow paths adjacent up-and downstream thereof (FIG. 6B) and a state where the flow path is hardly throttled (FIG. 6C).

To be specific, this operable throttle portion 50 includes a protrusion member 52 (corresponding to a protruding portion) provided so as to pass through an upper duct wall 43*pu* of the duct portion 43*p*, a protrusion member 52 (corresponding to a protruding portion) provided so as to pass through an lower duct wall 43*pd* of the duct portion 43*p*, and a drive mechanism (not shown) that drives the above pair of protrusion members 52, 52 to reciprocally move in the up-down direction that is a duct diameter direction of the duct portion 43*p*.

Each of the protrusion members 52 has a substantially cylindrical body with the direction of reciprocal movement as its axial direction, and one end portion 52*a* of both end portions, which is positioned inside the flow path, is formed into a hemispherical shape. Further, these protrusion members 52, 52 are reciprocally moved by the drive mechanism while keeping each of protruding length L52*a*, L52*a* of the hemispherical end portions 52*a*, 52*a* into the flow path in the same state with each other. Therefore, when the protrusion members 52, 52 reaches a protrusion limit in FIG. 6B, the sectional shape of the flow path is throttled at the central portion of the CD direction, resulting in making the above central portion into a constricted shape in the up-down direction. On the other hand, when the protrusion members 52, 52 reaches a retraction limit in FIG. 6C, the sectional shape of the flow path is hardly throttled and is a substantially perfect circular shape that is an approximately original shape of the duct portion 43*p*.

Figure 7A:
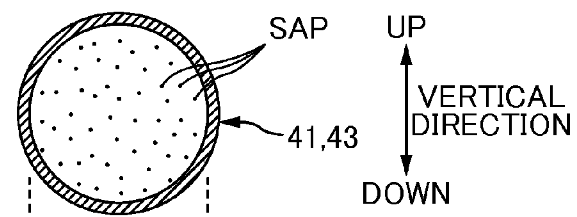
FIGS. 7A to 7*c* are diagrams explaining the reasons that the discharge distribution in the CD direction of SAP can be changed by an operable throttle portion 50 provided with a protrusion member 52.
Figure 7B:
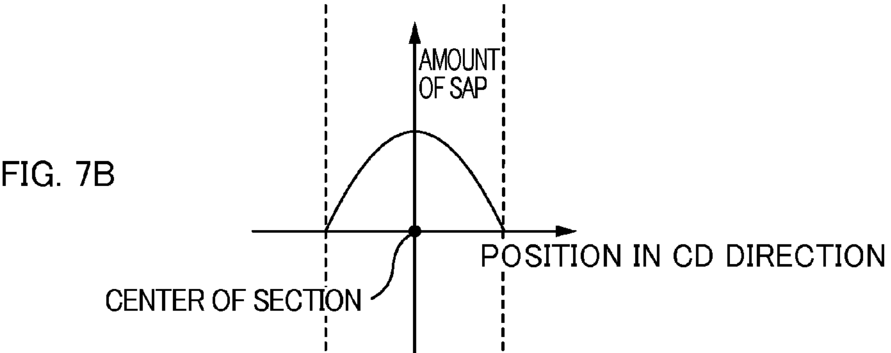
Figure 7C:
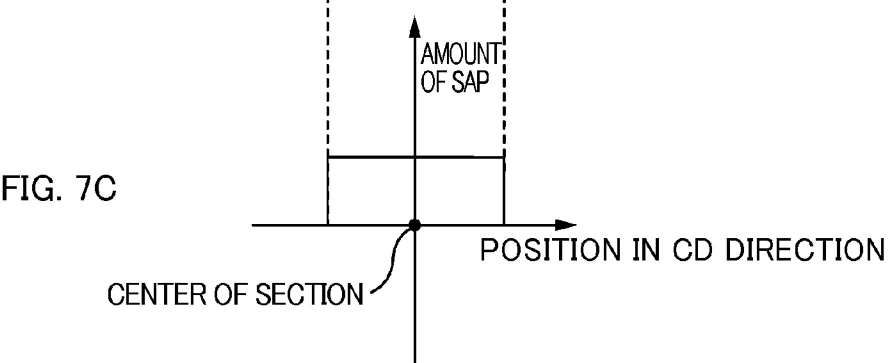

In this way, the discharge distribution in the CD direction of SAP can be changed into both distributions that are the substantially uniform distribution in the CD direction and the distribution being denser at the central portion of the CD direction. FIGS. 7A to 7C are explanatory diagrams for this reason.

In this example, the horizontal duct portion 43 of the polymer discharge tube 41 is a circular pipe as stated above. Therefore, the sectional shape of the flow path thereof (i.e., an imaginary plane with the direction of flow through the flow path as the normal direction) is a perfect circular shape as shown in FIG. 7A. Accordingly, when the distribution of the amount of SAP is seen relating to the CD direction as shown in FIG. 7B in a state where SAP is uniformly distributed in the section of the flow path as shown in FIG. 7A, the amount of SAP at the center of the CD direction is larger than both sides thereof due to the perfect circular sectional shape of the polymer discharge tube 41. That is, SAP is collected at the center of the CD direction to form the distribution being dense at the center. Therefore, when the protrusion members 52, 52 are positioned at the retraction limit as shown in FIG. 6C, SAP is discharged from the discharge hole with the discharge distribution being denser at the center of the CD direction.

On the other hand, when the protrusion members 52, 52 are positioned at the protrusion limit as shown in FIG. 6B, the sectional shape of the flow path at the central portion of the CD direction becomes constricted. Therefore, the distribution being dense at the central portion of the CD direction, which is created when the aforementioned sectional shape of the flow path is a perfect circular shape, is set off by the action of the diverted flow due to the constricted shape of the aforementioned central portion of the CD direction. More specifically, the space of the parts at the both sides (two end sides) of the above central portion is wider than the space of thereof in the up-down direction. Therefore, when SAP pass through the position of the protrusion members 52, 52, the amount of SAP at the central portion of the CD direction is reduced and that at the parts at the both sides are increased. In this way, the discharge distribution in the CD direction of SAP becomes a substantially uniform distribution along the CD direction as shown in FIG. 7C.

Note that, as shown in FIGS. 6A to 6C, seal members 54 having a through hole 54*h* in the up-down direction are fixed on the outer circumferential face of the duct portion 43*p*, and the protrusion member 52 is passed through the aforementioned through hole 54*h*, thereby surrounding the entire circumference of the outer circumferential face of the protrusion member 52. In this way, leakage of SAP or air 6 to the outside of the duct portion 43*p* may be prevented.

Such a pair of the protrusion members 52, 52 is reciprocally moved in the up-down direction in conjunction with, that it, in synchronization with the travel of the forming die 21. For example, the protrusion members 52, 52 are driven by the drive mechanism so as to perform one reciprocation motion for each forming die 21 in response to when each of the forming dies 21 passes by the duct 31. In this way, SAP is discharged toward the crotch corresponding portion 21*c* as the central portion 21*c* of the circumferential direction Dc in the forming die 21 with the distribution being dense at the center in the CD direction as shown in FIG. 7B. On the other hand, SAP is discharged toward the front body corresponding portion 21*e* and the back body corresponding portion 21*e* as the both end portions 21*e*, 21*e* in the above circumferential direction Dc with the substantially uniform distribution along the CD direction as shown in FIG. 7C.

Thus, the drive mechanism that drives the protrusion members 52, 52 includes, for example, a servo motor, a motion conversion mechanism such as a crank mechanism or cam mechanism which converts a rotational movement of the rotational axis of the servo motor into a reciprocating motion to transfer it to the protrusion member 52, a sensor that outputs a synchronizing signal to synchronize the travel of the forming die 21 and the drive of the protrusion member 52, and a controller that controls the servo motor on the basis of the above-mentioned synchronizing signal.

The sensor is, for example, a rotary encoder. And, the sensor detects a rotation angle of the rotating drum 20 as an alternative to the travel of the forming die 21, and outputs this detected signal as a synchronizing signal to the controller.

Further, the controller is, for example, a programmable logic controller, and includes a processor and memory. Then, the controller controls the servo motor on the basis of the synchronizing signal of the encoder by allowing the processor to read out a program from the memory and execute the program. Thereby, the protrusion members 52, 52 are allowed to reciprocate in synchronization with the travel of each of the forming dies 21.

More specifically, for example, the encoder makes one revolution along with every rotational movement of the rotating drum 20, which covers a set pitch P21 of the forming die 21. Then, during this one revolution, an angular signal between 0 degree and 360 degrees is outputted as the above-mentioned synchronizing signal in proportion to the magnitude of the rotational movement of the rotating drum 20. In this example, since six forming dies 21 are provided along the circumferential direction Dc, the encoder outputs an angular signal between 0 degree and 360 degrees along with every rotational movement covering 60 degrees of the rotating drum. On the other hand, the controller that received this angular signal controls the rotation of the rotational axis of the servo motor so that the rotational angle becomes the same as the indicated value of this angular signal. In this way, an input axis of the crank of the crank mechanism as the motion conversion mechanism is allowed to make one revolution along with one revolution of the above rotational axis. As a result, the protrusion members 52, 52 connected to the crank perform one reciprocating motion each time the forming die 21 passes by the position of the duct 31.

Note that, the drive mechanism of the protrusion member 52 is not limited to above configuration.

For example, the rotational movement of the rotating drum may be used for driving the protrusion member 52 by connecting the rotational axis of the rotating drum 20 with the input axis of the above-mentioned crank mechanism at a predetermined ratio of rotation using an appropriate train of gears (in which a plurality of gears are engaged), an endless belt or the like. In this case, the above-mentioned ratio of rotation, that is, the ratio of rotation of the input axis of the crank mechanism with respect to the rotational axis of the rotating drum 20 is set to the same value as the number of forming dies 21 (in this example, “6”) on the outer circumferential face 20*a* of the rotating drum 20. In this way, each time the forming die 21 passes by the duct 31, the protrusion members 52, 52 are adapted to perform one reciprocating motion.

Furthermore, a cam mechanism may be used as the drive mechanism of the protrusion member 52. In this case, for example, a cam such as a plate cam is provided in an integrated manner with the rotational axis of the rotating drum 20, and a cam follower is coupled to the protrusion member 52. Then, the cam follower comes into contact with a cam face of the cam rotating in an integrated manner with the rotating drum 20, thereby allowing the cam follower to reciprocate based on the cam curve of the cam face and causing the protrusion members 52, 52 to reciprocate.

Figure 8A:
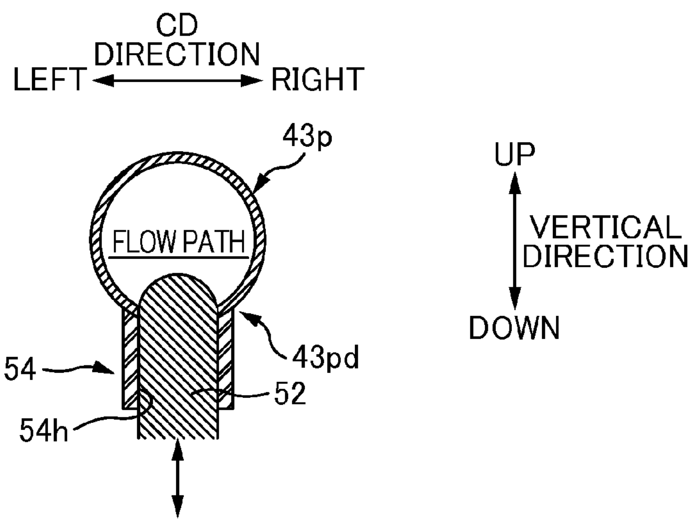
FIGS. 8A and 8B are cross-sectional views of other examples of the operable throttle portion 50 provided with the protrusion member 52.

Further, in some cases, the aforementioned protrusion member 52 may be provided to only one of the upper duct wall 43*pu* and lower duct wall 43*pd* in the duct portion 43*p*. And in this case where only one protrusion is provided, the protrusion member 52 is preferably provided on the lower duct wall 43*pd* as shown in FIG. 8A. This is because the SAP distribution in the up-down direction is assumed to be uneven such that the amount of SAP in the lower half of the space of the flow path is greater than that in the upper half of the space due to the own weight of SAP. Therefore it is understood that the protrusion member 52 provided at the lower duct wall 43*pd* would be more effective in contributing to separate the SAP flow into the right and left flows in the CD direction.

Further, the position where such protrusion members 52 are provided is not limited to the upper duct wall 43*pu* and lower duct wall 43*pd* of the duct portion 43*p*, and the protrusion members 52 may also be provided at an another appropriate position in accordance with individual circumstances of the fiber stacking device 10.

Figure 8B:
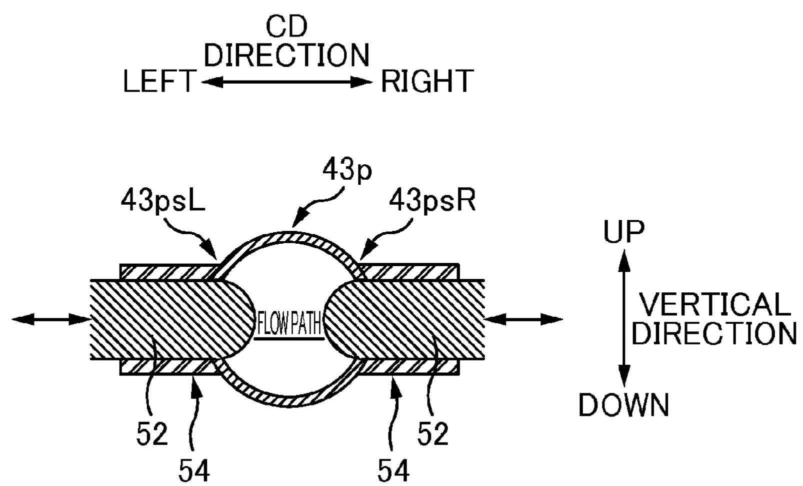

For example, as shown in a cross-sectional view of FIG. 8B, the protrusion members 52, 52 may be provided to each of a left part duct wall 43*ps*L and right part duct wall 43*ps*R of the duct portion 43*p* of the polymer discharge tube 41. Note that, in this case, each of the protrusion members 52, 52 horizontally reciprocate in a left-right lateral direction. According to this configuration, the discharge distribution in the CD direction of SAP can be changed from the distribution being dense at the central portion of the CD direction to the distribution being much denser at the central portion by moving the protrusion members 52, 52 from the retraction limit to the protrusion limit. In some cases, it is a matter of course that such protrusion members 52 may be provided to only one of the left part duct wall 43*ps*L and the right part duct wall 43*ps*R.

Figure 9:
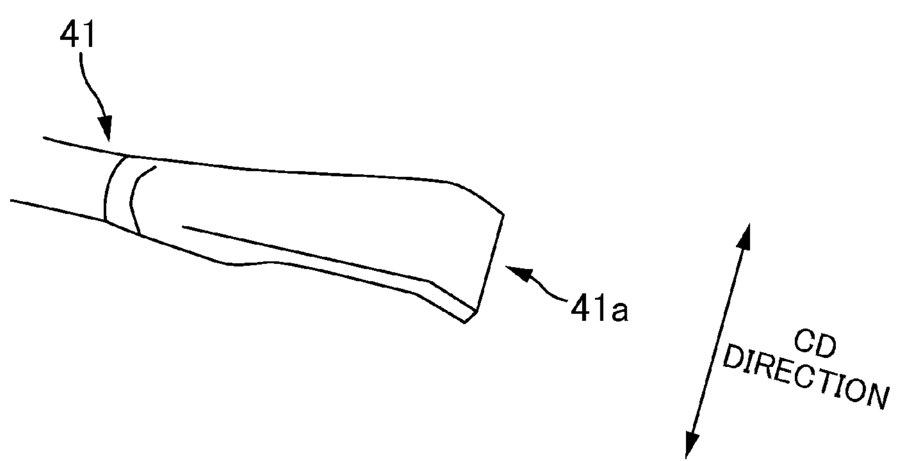
[FIG. 9]

Desirably, it is preferable that the shape of the flow path from the operable throttle portion 50 to the discharge hole 41*a* on the downstream side thereof shown in FIG. 4 is a shape that is capable of maintaining the discharge distribution in the CD direction formed by this operable throttle portion 50 as much as possible. FIG. 9 is an example thereof showing a perspective view of a portion proximate the discharge hole 41*a* of the polymer discharge tube 41, and the flow path in the examples shown in this FIG. 9 and FIG. 4 has a flattened sectional shape in the CD direction. To be more specific, the flow path is formed such that the dimensions in the up-down direction (vertical direction) is reduced stepwise or continuously toward the discharge hole 41*a* or the dimension in the CD direction is increased stepwise or continuously toward the discharge hole 41*a* thereby forming the flow path to have an approximately rectangular sectional shape flattened with the dimension in the up-down direction of the flow path being smaller than that in the CD direction. And at the tip thereof, the aforementioned discharge hole 41*a* is provided. Note that this discharge hole 41*a* also has a sectional shape flattened in the CD direction, to be specific, the shape of the opening portion is approximately rectangular with the CD direction as its longitudinal direction.

Here, it is preferable that the dimension of the discharge hole 41*a* in the CD direction is equal to or larger than the inner diameter of the polymer discharge tube 41 and equal to or smaller than the dimension of the absorbent body 1 in the CD direction. Further, it is preferable that the area of the discharge hole 41*a* is set so as to be equal to or smaller than the sectional area of the polymer discharge tube 41.

Such shapes of the flow paths with a flattened sectional shape is formed by, for example, collapsing the portion proximate the discharge hole 41*a* of the polymer discharge tube 41 in the up-down direction while widening in the CD direction to have a flattened tubular shape (FIGS. 9 and 4).

Figure 10A:
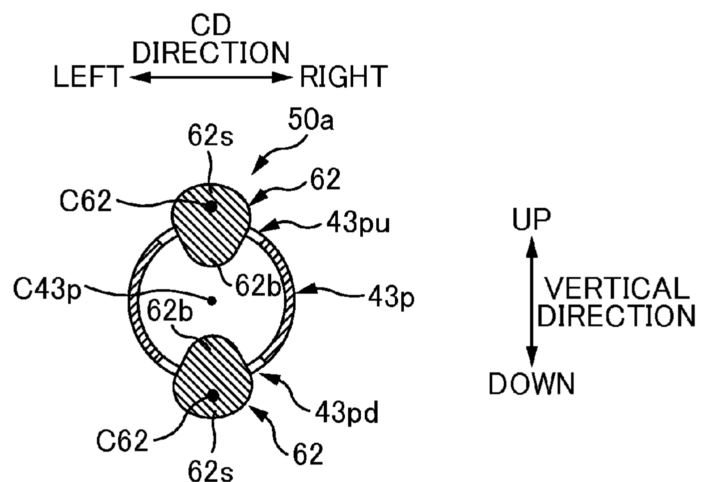
FIGS. 10A and 10B are explanatory diagrams of a modified example of an operable throttle portion 50*a* in the first embodiment.
Figure 10B:
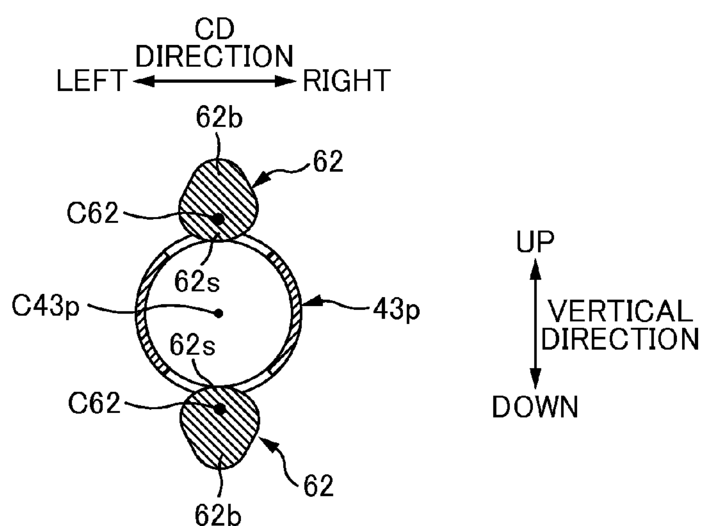

FIGS. 10A and 10B are explanatory diagrams of the operable throttle portion 50*a* in the modified example of the first embodiment. In the first embodiment, the protrusion members 52, 52 reciprocate in the same straight line along the up-down direction, so that the discharge distribution in the CD direction of SAP has been changed by changing the sectional shape of the flow path in the duct portion 43*p*. However, in this modified example, it is mainly different in that the sectional shape of the flow path is changed by rotating different diameter rotating members 62, 62 in a single direction. And the configurations other than the above are generally the same as those in the first embodiment. Therefore, differences between them will be mainly described hereinafter, and the description of the same content to the first embodiment is omitted.

The different diameter rotating member 62 has, for example, a disk member as its main body, and has portions 62*b*, 62*s* whose turning radius as a distance from its outer circumferential edge to a rotation center axis C62 are different with each other. In the example shown in FIGS. 10A and 10B, there is a large-diameter portion 62*b* in which the turning radius is largest and a small-diameter portion 62*s* in which the turning radius is smallest. The different diameter rotating member 62 is rotatably supported at the upper duct wall 43*pu* of the duct portion 43*p* of the operable throttle portion 50*a* with the rotation center axis C62 being oriented to the direction parallel to duct axis direction C43*p* of the duct portion 43*p*, while a part of the different diameter rotating member 62 enters into the flow path by passing through the aforementioned duct wall 43*pu* with keeping the above state. Further, a similar different diameter rotating member 62 is also provided to the lower duct wall 43*pd* of the duct portion 43*p*. This different diameter rotating member 62 also has a part which enters into the flow path by passing through the duct wall 43*pd*.

Such a different diameter rotating member 62 is to reach a protrusion limit state that is the most protruded state into the flow path, when in a state as shown in FIG. 10A, that is, in a state where the large-diameter portion 62*b* faces toward the center C43*p* of the section of the duct portion 43*p*. On the other hand, the different diameter rotating member 62 is to reach a retraction limit state that is the most retracted state from the inside of the flow path when in a state as shown in FIG. 10B, that is, in a state where the small-diameter portion 62*s* faces toward the center c43*p* of the section of the duct portion 43*p*. And in this example, these large-diameter portion 62*b* and small-diameter portion are inversely positioned relative to one another across each of the rotation center axes C62. That is, these two portions have a 180-degree phase shift with respect to each other in the rotational direction. Therefore, when the different diameter rotating member 62 makes one revolution, each of the above-mentioned protrusion limit state and retraction limit state occurs once while shifting their phases by 180 degrees. As a result, the change of the discharge distribution which is similar to the case of the aforementioned first embodiment can be realized by the operable throttle portion 50*a* in the modified example as well.

Note that, a configuration in which a motion conversion mechanism (crank mechanism) is simply omitted from the drive mechanism in the above-mentioned first embodiment can be exemplified as the drive mechanism in the above example. More specifically, when a rotation center axis C62 of the different diameter rotating member 62 is connected coaxially with the rotational axis of the servo motor by using an appropriate shaft coupling, the above-mentioned drive mechanism in the first embodiment can be applied as the drive mechanism of the different diameter rotating member 62 associated with this modified example in a state where the configurations other than the above is maintained without any change. Therefore, the description thereof is omitted.

===Second Embodiment===

Figure 11A:
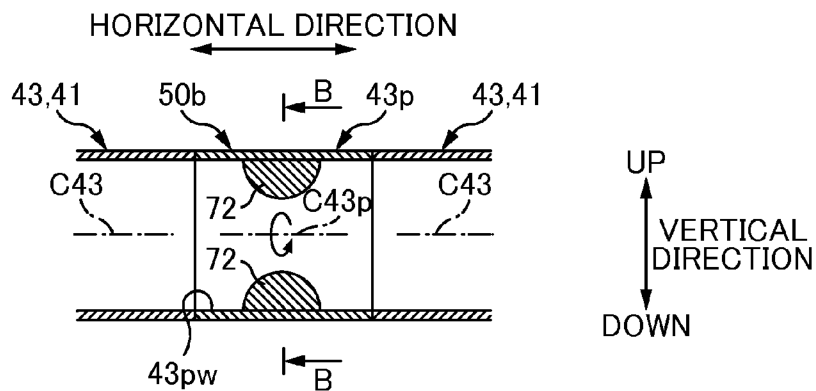
FIGS. 11A to 11C are explanatory diagrams of the operable throttle portion 50*b* in the second embodiment.
Figure 11B:
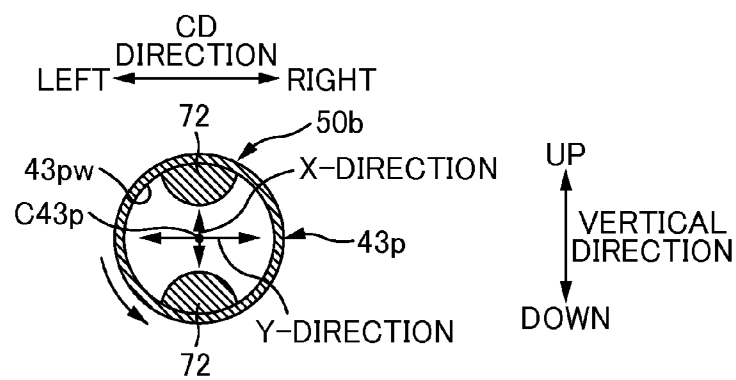
Figure 11C:
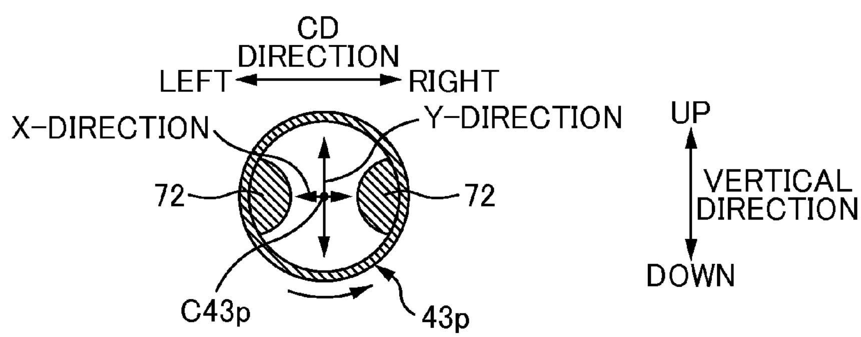

FIGS. 11A to 11C are explanatory diagrams of the operable throttle portion 50*b* in the second embodiment. FIG. 11A is a view corresponding to the enlarged view of part VI in FIG. 4, FIG. 11B is a cross-sectional view taken along line B-B of FIG. 11A. Further, FIG. 11C is a cross-sectional view taken along line B-B of FIG. 11A in a different state from that of FIG. 11B.

In the aforementioned first embodiment and modified example thereof, the discharge distribution in the CD direction of SAP has been changed by changing the protruding length of the protrusion members 52 or the different diameter rotating members 62 into the flow path to change the sectional shape of the flow path. However, the second embodiment is different from the above described embodiments in that the discharge distribution is changed by fixing the sectional shape of the flow path to the shape other than the perfect circular shape without changing the sectional shape of the flow path of the duct portion 43*p* of the operable throttle portion 50*b*, and by rotating the duct portion 43*p* about the duct axis C43*p*. Note that, the other configurations are generally the same as those in the above-mentioned embodiments. Therefore, differences between them will be mainly described hereinafter, and the description of the similar content to the first embodiment is omitted.

As shown in FIGS. 11A and 11B, the duct portion 43*p* of the operable throttle portion 50*b* is, for example, a short pipe member having the same inner diameter as the polymer discharge tube 41 and a predetermined length in the duct axis direction C43*p*. On the other hand, in the polymer discharge tube 41, a part of the duct portion thereof is removed, and the aforementioned duct portion 43*p* of the operable throttle portion 50*b* is interposed at the position of the removed duct portion with the duct axis C43*p* thereof aligned with the duct axis C43 of the polymer discharge tube 41. In this interposed state, the duct portion 43*p* of the operable throttle portion 50*b* is rotatably guided and supported about the duct axis C43*p* by an appropriate guide member (not shown) provided at the discharge tube 41 while the flow path of the duct portion 43*p* is communicated with the flow path of the polymer discharge tube 41.

Further, a pair of protrusions 72, 72 protruding inward in the tube diameter direction is immovably provided on the inner wall face 43*pw* the duct portion 43*p* in a substantially integrated manner, with the protrusions facing each other. In this way, the sectional shape of the flow path of this duct portion 43*p* is a substantially gourd shape having a constricted portion at the center C43*p* thereof. Here, for convenience of explanation, when a constricted direction of the substantially gourd shape is defined as a X-direction, and a longitudinal direction of the substantially gourd shape, which is orthogonal to the constricted direction, is defined as a Y-direction as shown in FIG. 11B, the X-direction and Y-direction face to the up-down direction, the CD direction (horizontal direction), or the direction between those two directions in accordance with the rotation of the duct portion 43*p*. As shown in FIG. 11B, the state in which the X-direction faces to the up-down direction becomes substantially the same state as that of the protrusion limit (FIG. 6B) in the aforementioned first embodiment. Therefore, in this state, SAP is discharged in the CD direction in the substantially uniform distribution. On the other hand, as shown in FIG. 11C, when the X-direction faces to the CD direction, the sectional shape of the flow path narrows in the CD direction as a whole. Thereby, SAP is to be gathered at the center of the CD direction, so that SAP is discharged with the distribution being dense at the center of the CD direction. That is, with this operable throttle portion 50*b*, the discharge distribution in the CD direction of SAP can be changed by rotating the duct portion 43*p* about the duct axis C43*p*.

The drive mechanism that rotates this duct portion 43*p* includes, for example, a servo motor, a rotational movement transmitting mechanism that transmits a rotational movement of the rotational axis of the servo motor to the duct portion 43*p*, a sensor that outputs a synchronizing signal to synchronize the travel of the forming die 21 and the drive of the duct portion 43*p*, and a controller that controls the servo motor on the basis of the above-mentioned synchronizing signal.

The above-mentioned sensor, servomotor, controller and the like can be the same ones as in the first embodiment. On the other hand, a train of gears, wrapping connector transmission device (a mechanism using an endless belt and pulley) and the like can be exemplified as the rotational movement transmitting mechanism.

Note that, in the example of FIG. 11B, the sectional shape of the flow path of the duct portion 43*p* of the operable throttle portion 50*b* has been a substantially gourd-shape. However, this sectional shape is not limited thereto. That is, the shape other than the substantially gourd-shape may also be used in accordance with individual circumstances of the fiber stacking device 10. However, when the sectional shape of the flow path is a perfect circular shape, the sectional shape of the flow path does not vary even if the duct portion 43*p* is rotated about the duct axis C43*p*. Therefore, in order to change the discharge distribution, the sectional shape needs to be a shape other than the perfect circular shape. Such a sectional shape of the flow path is appropriately set by taking into consideration individual circumstances of the fiber stacking device 10.

===Other Embodiments===

Hereinabove, explanation on the embodiments of the present invention have been given. However, the present invention is not limited to such embodiments and modifications such as those in the following can be made.

In the above-mentioned embodiment, SAP has been exemplified as an example of particulate matter. However, the invention is not limited thereto. Particulate matter having a function other than fluid absorption such as granular activated carbon for deodorization may also be used.

In the aforementioned first embodiment, as shown in FIGS. 6A to 6C, the hemispherical shape has been shown as an example of the shape of the end portion 52*a* of the protrusion member 52 to be provided for the operable throttle portion 50. However, the shape of the end portion 52*a* is not limited thereto. For example, the shape can be pyramidal such as a triangular pyramid or a circular cone, or also be conical such as a triangular prism or a cylinder, or a unique shape having a plurality of different curved surfaces and planes combined. Further, the substantially cylindrical body has been exemplified as the protrusion member 52; however, the invention is not limited thereto. For example, a prismatic body whose sectional shape is a polygonal shape may be used, and a board type or a spherical body may also be used.

In the above-mentioned embodiment, the polymer discharge tube 41 was configured with a circular pipe having a perfect circular sectional shape. However, the configuration is not limited thereto, and any configuration can be applied as long as a tubular member. For example, a pipe whose section is a polygonal shape such as a square pipe or a circular pipe whose section is such as an ellipsoidal shape can be used.

In the above-mentioned embodiment, the operable throttle portions 50, 50*a*, 50*b* are provided outside the duct 31. However, the locations at which those throttle portions are set are not limited thereto and the operable throttle portions may be provided inside the duct 31. However, when the operable throttle portions are provided inside the duct 31, maintenance and inspection of the operable throttle portions 50, 50*a*, 50*b* and their drive mechanism become more difficult to be performed. In addition, since the protrusion member 52, the different diameter rotating member 62 and the like which are operable portions of the operable throttle portions 50, 50*a* protrude outwardly from the polymer discharge tube 41 as shown in FIGS. 6B and 10A, there is a risk that the movements of these protrusion members 52, different diameter rotating members 62 and the like affect the airflow 3 in the duct 31 and disturb the deposition of the pulp fiber 2. Therefore, it is preferable that the operable throttle portions 50, 50*a*, 50*b* are provided outside the duct 31.

In the above-mentioned embodiment, the operable throttle portions 50, 50*a*, 50*b* were provided only at one location in the duct axis direction of the polymer discharge tube 41; however, the location is not limited to one, and the operable throttle portions may be provided at a plurality of locations in the duct axis direction.

In the above-mentioned embodiment, the forming die 21 formed on the outer circumferential face 20*a* of the rotating drum 20 in the depressed form is shown as an example of the deposit portion. However, the deposit portion is not limited thereto. For example, the outer circumferential face 20*a* configured to have a generally smooth surface with suction force acting only in this predetermined area of this outer circumferential area 20*a* can be used to form absorbent bodies 1 by depositing pulp fibers 2 and SAP at this predetermined area as the aforementioned deposit portion. Further, a chain conveyor or a belt conveyor and the like can be used instead of the rotating drum 20. In other words, the forming die 21 can be made to travel in a predetermined circumferential orbit (corresponding to the travel path) with a corresponding conveyor while the aforementioned duct 31 is positioned at a predetermined position on the circumferential orbit.

In the above-mentioned embodiment, pulp fiber 2 (pulp pulverized into fibrous form) was exemplified as liquid absorbent fiber; however, various material used for the absorbent body 1 of absorbent articles such as conventional sanitary napkins, disposable diapers and the like can be used as this liquid absorbent fiber without special requirements. For example, cellulosic short fiber such as rayon fiber and cotton fiber or synthetic short fiber such as polythene fiber and the like can be used. These fibers can be used alone or, two types or more of them combined.

In the above-mentioned embodiment, specific examples of superabsorbent polymer (SAP) were not described. However, various material used for the absorbent body 1 of absorbent articles such as conventional sanitary napkins, disposable diapers and the like can be used as this SAP without special requirements. For example, starch material, cellulosic material, synthetic polymer material and the like can be used. Here, SAP is generally in a particle form. As SAP, it is preferable that it is liquid absorbing and retentive of 20 times or more of its own weight and having a characteristic of gelation as well. For example, starch-acrylic acid (sodium) grafted copolymer, saponifiable material of starch-acrylonitrile copolymer, cross-linked sodium carboxymethyl cellulose, acrylic acid (sodium) polymer and the like are preferable. The above SAP can be used alone or, two types or more of them combined.

In the above-mentioned embodiment, air 3, 6 were exemplified as examples of the first gas and the second gas. However, the invention is not limited thereto. That is, as long as gas can be a medium for transferring liquid absorbent fiber such as pulp fiber, and particulate matter such as SAP, and does not cause chemical reaction with these liquid absorbent fiber and particulate matter, the gas need not be air and for example, nitrogen can be used.

In the above-mentioned embodiment, the duct 31 that is continuous in the vertical direction was positioned above the rotating drum 20, and its distribution opening 31*a* was made to cover the outer circumferential face 20*a* of the rotating drum 20 from above so that the flow path of the airflow 3 including pulp fiber 2 was formed to extend in vertical direction. However, the invention is not limited thereto. For example, a duct 31 that is continuous in a horizontal or a diagonal direction to the MD direction can be arranged with the flow path of the airflow 3 formed in the horizontal or diagonal direction.

REFERENCE SIGNS LIST

1 absorbent body,
1*c* central portion (crotch corresponding portion), 1*e* both end portions (back body corresponding portion, front body corresponding portion),
2 pulp fiber (liquid absorbent fiber), 2*s* pulp sheet,
3 airflow (first gas, air), 6 airflow (second gas, air),
9 sheet form member,
10 fiber stacking device (manufacturing device),
20 rotating drum, 20*a* outer circumferential face,
21 forming die (deposit portion),
21*c* central portion (crotch corresponding portion), 21*e* both end portions (back body corresponding portion, front body corresponding portion),
22 air intake hole, 27*a* partition wall, 27*b* partition wall,
31 duct, 31*a* distribution opening, 31*b* opening at upper end,
35 pulverizer,
41 polymer discharge tube (particulate matter discharge tube),
41*a* discharge hole, 41*e* tip end,
42 vertical duct portion, 42*a* upper end, 42*b* substantially middle position,
43 horizontal duct portion,
43*p* duct portion, 43*pu* duct wall, 43*pd* duct wall,
43*ps*L duct wall, 43*ps*R duct wall,
43*pw* inner wall face,
44 bend duct,
46 SAP feed mechanism, 47 screw feeder,
48 compressed air injection device, 48*a* pipe, 48*b* valve,
50 operable throttle portion, 50*a* operable throttle portion, 50*b* operable throttle portion,
52 protrusion member (protruding portion), 52*a* hemispherical end portion,
54 seal member, 54*h* through hole,
62 different diameter rotating member, 62*b* large-diameter portion, 62*s* small-diameter portion,
72 protrusion,
81 belt conveyor, 83 suction box,
SAP superabsorbent polymer (particulate matter),
R1 first region, R2 second region, Z1 zone, Z2 zone,
C20 rotational axis, C43 duct axis, C43*p* duct axis, C62 rotation center axis,
Tr20 circumferential path (travel path)

The invention claimed is:

1. A device for manufacturing an absorbent body, said device comprising:
- a deposit portion configured to travel along a predetermined travel path;
- a duct configured to distribute liquid absorbent fiber in a first gas on the deposit portion from a distribution opening placed opposing the travel path;
- a particulate matter discharge tube having a tip end thereof being introduced into the duct, and configured to discharge a second gas having particulate matter mixed therein from a discharge hole of the tip end;
- an operable throttle portion configured to throttle a flow path of the particulate matter discharge tube to change discharge distribution of the particulate matter; and
- a drive mechanism, wherein
- the operable throttle portion is configured to be operated in conjunction with the travel of the deposit portion,
- the operable throttle portion is provided at a duct portion of the particulate matter discharge tube,
- the operable throttle portion includes
  - a first protrusion member configured to pass through a first duct wall of the duct portion; and
  - a second protrusion member configured to pass through a second duct wall of the duct portion, and
- the drive mechanism is configured to drive the first protrusion member and the second protrusion member to reciprocally move along a duct diameter direction of the duct portion.

2. The device according to claim 1, wherein
- a plurality of the deposit portions is configured to travel at a predetermined pitch along the travel path,
- the operable throttle portion is configured to repeat a given unit motion each time the deposit portion passes by the position of the duct.

3. The device according to claim 1, wherein
the operable throttle portion is provided outside the duct.

4. The device according to claim 1, wherein each of the first protrusion member and the second protrusion member has a substantially cylindrical body having an axial direction coinciding with the duct diameter direction.

5. The device according to claim 4, wherein
- the substantially cylindrical body has two end portions,
- one of the two end portions is positioned inside the flow path of the particulate matter discharge tube, and has a hemispherical shape.

6. The device according to claim 5, wherein the first protrusion member and the second protrusion member are configured to be reciprocally moved by the drive mechanism while having same protruding lengths of the corresponding hemispherical end portions into the flow path of the particulate matter discharge tube.

7. The device according to claim 5, wherein
- when the first protrusion member and the second protrusion member are moved to reach corresponding protrusion limits, a sectional shape of the flow path at a central portion of the particulate matter discharge tube in a cross direction perpendicular to the flow path is throttled, and the central portion of the particulate matter discharge tube is in a constricted shape, and
- when the first protrusion member and the second protrusion member are moved to reach corresponding retraction limits, the sectional shape of the flow path is a substantially circular shape coinciding with a sectional shape of the duct portion.

8. A method of manufacturing an absorbent body, said method comprising:
- causing a deposit portion to travel along a predetermined travel path;
- distributing liquid absorbent fiber in a first gas on the deposit portion from a distribution opening of a duct placed opposing the travel path;

discharging particulate matter mixed in a second gas from a discharge hole of a tip end of a particulate matter discharge tube, the tip end being introduced into the duct; and operating an operable throttle portion in conjunction with the travel of the deposit portion, the operable throttle portion throttling a flow path of the particulate matter discharge tube to change discharge distribution of the particulate matter, wherein the operable throttle portion is provided at a duct portion of the particulate matter discharge tube, and the operable throttle portion includes a first protrusion member configured to pass through a first duct wall of the duct portion, and a second protrusion member configured to pass through a second duct wall of the duct portion, and said operating includes reciprocally moving the first protrusion member and the second protrusion by a drive mechanism along a duct diameter direction of the duct portion.

9. The method according to claim 8, further comprising:

causing a plurality of the deposit portions to travel at a predetermined pitch along the travel path, wherein, at said operating, the operable throttle portion repeats a given unit motion each time the deposit portion passes by the position of the duct.

10. The method according to claim 8, wherein the operable throttle portion is provided outside the duct.

11. The method according to claim 8, wherein each of the first protrusion member and the second protrusion member has a substantially cylindrical body having an axial direction coinciding with the duct diameter direction.

12. The method according to claim 11, wherein the substantially cylindrical body has two end portions, one of the two end portions is positioned inside the flow path of the particulate matter discharge tube, and has a hemispherical shape.

13. The method according to claim 12, wherein, at said operating, the first protrusion member and the second protrusion member are reciprocally moved by the drive mechanism while having same protruding lengths of the corresponding hemispherical end portions into the flow path of the particulate matter discharge tube.

14. The method according to claim 12, wherein when the first protrusion member and the second protrusion member are moved to reach corresponding protrusion limits, a sectional shape of the flow path at a central portion of the particulate matter discharge tube in a cross direction perpendicular to the flow path is throttled, and the central portion of the particulate matter discharge tube is in a constricted shape, and when the first protrusion member and the second protrusion member are moved to reach corresponding retraction limits, the sectional shape of the flow path is a substantially circular shape coinciding with a sectional shape of the duct portion.

* * * * *